(12) United States Patent
Wang et al.

(10) Patent No.: US 8,344,102 B2
(45) Date of Patent: Jan. 1, 2013

(54) NANOPARTICLE AND MAGNETIC RESONANCE IMAGING CONTRAST AGENT

(75) Inventors: Yun-Ming Wang, Hsinchu (TW); Ting-Jung Chen, Yongkang (TW)

(73) Assignee: National Chiao Tung University, Hsinchu (TW)

( * ) Notice: Subject to any disclaimer, the term of this patent is extended or adjusted under 35 U.S.C. 154(b) by 283 days.

(21) Appl. No.: 12/760,396

(22) Filed: Apr. 14, 2010

(65) Prior Publication Data

US 2011/0092672 A1    Apr. 21, 2011

(30) Foreign Application Priority Data

Oct. 20, 2009   (TW) ................ 98135414 A

(51) Int. Cl.
| | | |
|---|---|---|
| *A61K 38/04* | (2006.01) | |
| *C07K 5/00* | (2006.01) | |
| *C07K 7/00* | (2006.01) | |
| *C07K 16/00* | (2006.01) | |
| *C07K 17/00* | (2006.01) | |
| *C07F 7/02* | (2006.01) | |

(52) U.S. Cl. .................................... 530/329; 546/14
(58) Field of Classification Search ................ None
See application file for complete search history.

(56) References Cited

U.S. PATENT DOCUMENTS

2006/0142749 A1* 6/2006 Ivkov ....................... 606/27
2009/0099282 A1* 4/2009 Muller et al. ............ 524/100

\* cited by examiner

*Primary Examiner* — Marcela M Cordero Garcia
(74) *Attorney, Agent, or Firm* — Osha • Liang LLP

(57) ABSTRACT

A nanoparticle contains a core including superparamagnetic nanoparticles and having an outer surface, and siloxanyl moieties covalently coupled to the outer surface of the core and having Formula (I):

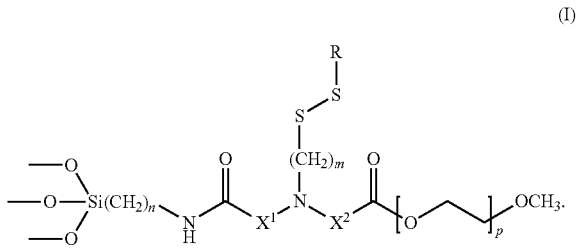

In formula (I): $X^1$ and $X^2$ independently represent methylene, ethylene or propylene; R represents an optionally substituted pyridyl group, or —S—R is a group derived from a targeting ligand containing —SH group and effective to bind specifically with a predetermined targeted cell in an object; n and m independently represent an integer ranging from 1 to 3; and p represents an integer ranging from 9 to 45. The nanoparticles are suitable for use as a magnetic resonance imaging contrast agent.

8 Claims, 11 Drawing Sheets

NANOPARTICLE AND MAGNETIC RESONANCE IMAGING CONTRAST AGENT

CROSS-REFERENCE TO RELATED APPLICATION

This application claims priority of Taiwanese Application No. 098135414, filed on Oct. 20, 2009.

BACKGROUND OF THE INVENTION

1. Field of the Invention

This invention relates to a nanoparticle, more particularly to a superparamagnetic nanoparticle suitable for use in magnetic resonance imaging (MRI) diagnosis.

2. Description of the Related Art

Nanoparticles, especially magnetic nanoparticles, may have a contrast enhancing effect for MRI diagnosis under a magnetic field. For example, ultrasmall superparamagnetic iron oxide nanoparticles (USPIO) can considerably reduce the spin-spin relaxation time (T2) of protons of the targeted tissue under a magnetic field, thereby enhancing the contrast of a MRI image. Hence, USPIO has been widely used as a MRI contrast agent. In addition, USPIO can be also incorporated into magnetic field-guided drug delivery vehicles for cancer treatment.

However, when USPIO is used in vivo, the problems of self-aggregation and adsorption to plasma albumin of USPIO tend to occur due to the high specific surface area thereof. As a consequence, USPIO may be undesirably consumed by phagocytosis for macrophages and cannot be coupled to the targeted tissue.

Taiwanese patent publication No. 200808815 discloses a MRI contrast agent that has the following formula and that is prepared by bonding folic acid to the modified USPIO. The contrast agent in this publication was used to detect position of the cancer cell through targeting to the folic acid receptors on the cancer cell membrane.

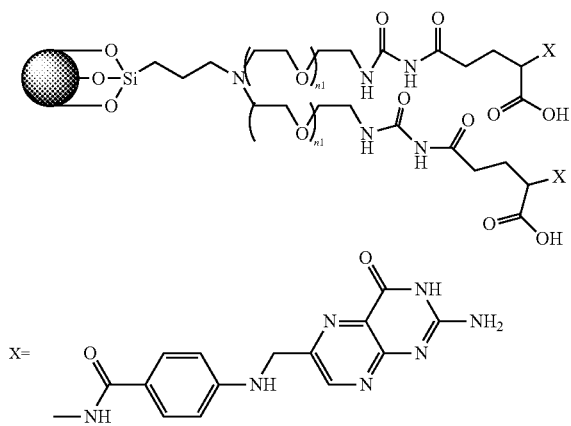

Although there have been researches on modifying the surface of USPIO to avoid self-aggregation and adsorption and on the use of targeting ligand in the nanoparticles to achieve a highly specific targeting to cancer cells, there is still a need in the art to find nanoparticles suitable for use as a contrast agent that has a greater effect on reducing T2 so as to accomplish higher sensitivity and good imaging effect.

SUMMARY OF THE INVENTION

Therefore, an object of the present invention is to provide nanoparticles that exhibit a highly specific targeting property and biocompatibility.

According to this invention, there is provided a nanoparticle that contains a core including superparamagnetic nanoparticles and having an outer surface, and siloxanyl moieties covalently coupled to the outer surface of the core and having Formula (I):

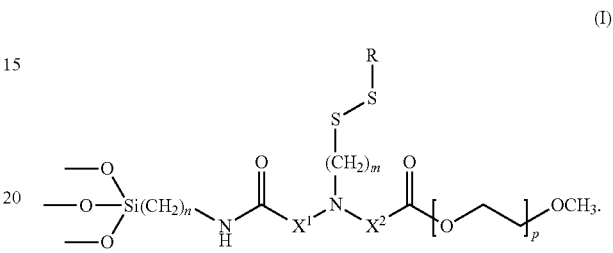

In Formula (I): $X^1$ and $X^2$ independently represent methylene, ethylene or propylene; R represents an optionally substituted pyridyl group, or —S—R is a group derived from a targeting ligand containing —SH group and effective to bind specifically with a predetermined targeted cell in an object; n and m independently represent an integer ranging from 1 to 3; and p represents an integer ranging from 9 to 45.

BRIEF DESCRIPTION OF THE DRAWING

Other features and advantages of the present invention will become apparent in the following detailed description of the preferred embodiments of this invention, with reference to the accompanying drawings, in which:

FIGS. 2(a)~(f) are TEM photos illustrating the appearance of USPIO prepared under different rotational speeds (300, 600 and 900 rpm) in Example 1 of this invention, in which FIGS. 2 (a), (b) and (c) are the photos prepared at 300, 600 and 900 rpm, respectively.

DETAILED DESCRIPTION OF THE PREFERRED EMBODIMENTS

Figure 1:
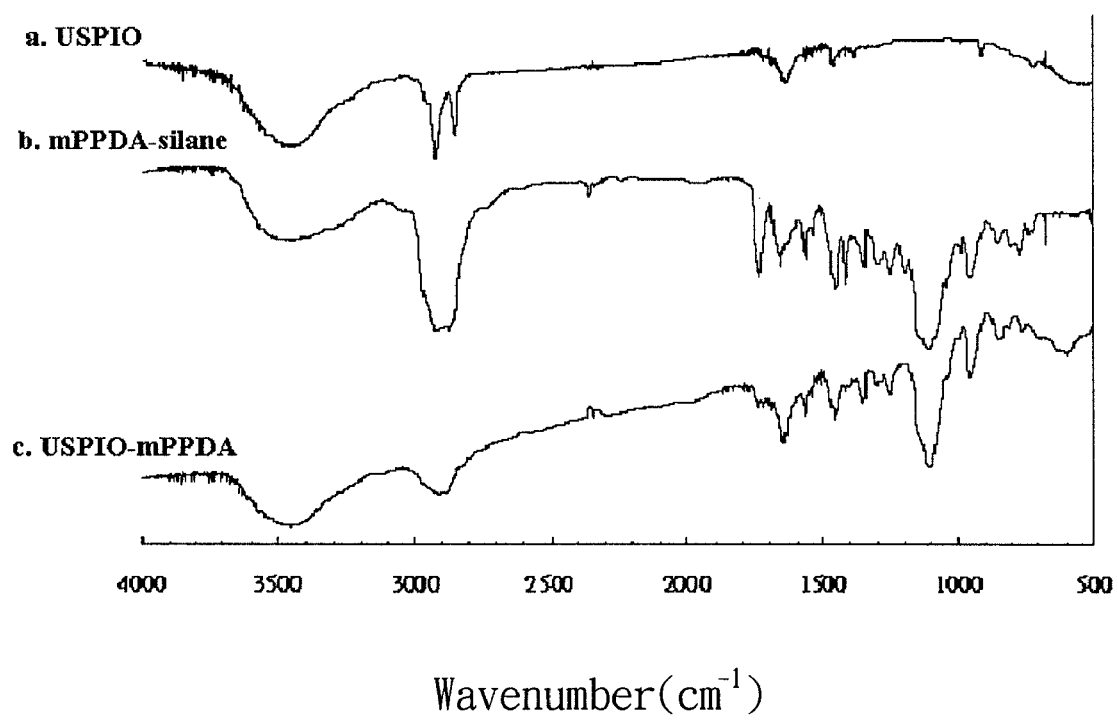
FIG. 1 shows FT-IR spectrums illustrating the functional groups in the structure of USPIO, mPPDA-silane and USPIO-mPPDA prepared in Example 1 of this invention.

The invention provides a nanoparticle that contains a core including superparamagnetic nanoparticles and having an outer surface, and siloxanyl moieties covalently coupled to the outer surface of the core and having Formula (I):

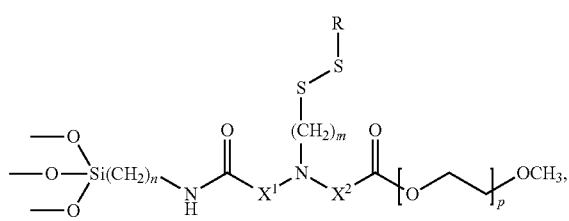

(I)

wherein, in Formula (I): $X^1$ and $X^2$ independently represent methylene, ethylene or propylene; R represents an optionally substituted pyridyl group, or —S—R is a group derived from a targeting ligand containing —SH group and effective to bind specifically with a predetermined targeted cell in an object; n and m independently represent an integer ranging from 1 to 3; and p represents an integer ranging from 9 to 45.

Preferably, the superparamagnetic nanoparticles are ultrasmall superparamagnetic iron oxide nanoparticles (USPIO).

In one aspect of this invention, R in Formula (I) represents an optionally substituted pyridyl group. Preferably, R is 2-pyridyl, 4-pyridyl, 5-methyl-2-pyridyl, 3-methyl-2-pyridyl, or 1-methyl-2-pyridyl.

In one preferred embodiment of this invention, $X^1$ and $X^2$ independently represent ethylene, R is 2-pyridyl and n=m=2, and the structure of Formula (I) is shown below:

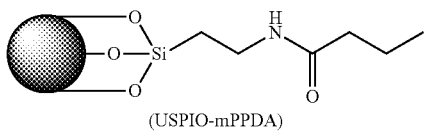

(USPIO-mPPDA)

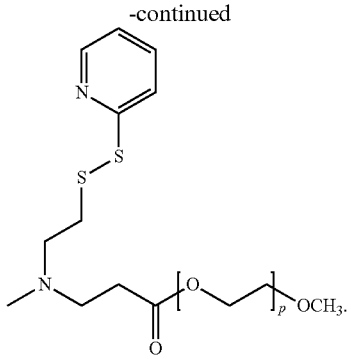

In another aspect of this invention, —S—R in Formula (I) is a group derived from a targeting peptide sequence, which may be designed or chosen according to the target of interest to be detected. Preferably, the targeting peptide sequence is interleukin 11 (IL-11), modified bombesin (BN) containing —SH group, or Cys-Lys-Gly-Arg-Gly-Asp (RGD-Cys, SEQ ID NO: 1).

In another preferred embodiment of this invention, $X^1$ and $X^2$ independently represent ethylene, —S—R is a group derived from RGD-Cys (SEQ ID NO: 1) and n=m=2, and the structure of Formula (I) is shown below.

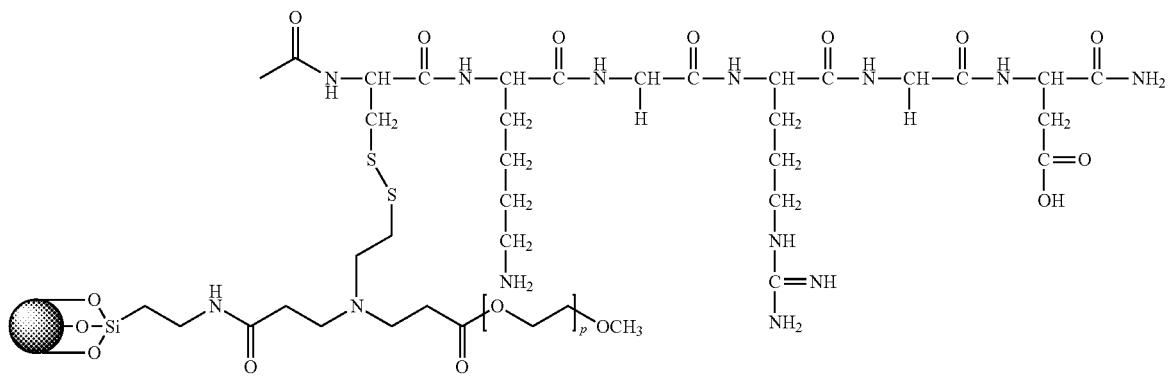

(USPIO-mPEG-RGD)

The nanoparticle of USPIO-mPPDA in the preferred embodiment of this invention is made according to the following steps: preparing USPIO, a modified siloxane, a modified polyethylene glycol (PEG) and 2-(pyridyldithio)-ethylamine (PDA); subjecting the modified siloxane, the modified PEG and PDA to reaction to obtain a modified compound; and subjecting the modified compound and USPIO to reaction to obtain USPIO-mPPDA. The nanoparticle of USPIO-mPEG-RGD in the preferred embodiment of this invention is prepared by subjecting USPIO-mPPDA and RGD-Cys (SEQ ID NO: 1) to reaction to obtain USPIO-mPEG-RGD.

The nanoparticles of this invention are suitable for use as a magnetic resonance imaging contrast agent for detecting living cells or tissues by magnetic resonance imaging techniques.

The following examples and comparative examples are provided to illustrate the merits of the preferred embodiments of the invention, and should not be construed as limiting the scope of the invention.

EXAMPLE

Example 1

Preparation of USPIO-mPPDA

1. Preparation of USPIO

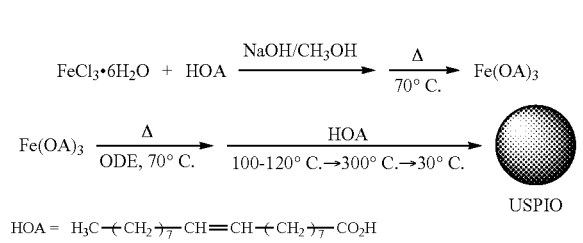

HOA = $H_3C\!-\!\!(CH_2)_{7}\!-\!CH\!=\!CH\!-\!(CH_2)_{7}\!-\!CO_2H$ 5.4 g (20 mmol) of $FeCl_3 \cdot 6H_2O$ and 17 mL (60 mmol) of oleic acid (HOA) were mixed with 100 mL of methanol to obtain an amber mixture. A solution containing 2.4 g (60 mmol) of NaOH and 200 mL of methanol was added dropwisely into the amber mixture and was then subjected to reaction with the amber mixture. The reaction was finished when the solution became turbid. The turbid solution underwent filtration to obtain a yellow precipitate. The yellow precipitate was washed with methanol, followed by heating until the temperature was raised to 70° C., and drying in a vacuum environment so as to obtain a brown wax of $Fe(OA)_3$.

3 g (3.3 mmol) of $Fe(OA)_3$ and 15 g (60 mmol) of 1-octadecene (ODE) were mixed under a stirring speed of 300 rpm and were heated until the temperature was raised to 70° C., after which 0.4 mL (1.6 mmol) of oleic acid was added therein to obtain a mixture. The mixture was heated to a temperature of 100~120° C. and was held at the temperature for 30 minutes for removing trace water, after which the mixture was cooled to room temperature, and was heated again at a rate of 3.3° C./min to raise the temperature to 300° C. for 90 minutes to allow a reaction to take place for 60 minutes at 300° C. The mixture was then cooled to 30° C. at a reducing rate of 20° C./min so as to obtain USPIO.

The FT-IR spectrum of the product thus obtained is shown in FIG. 1. An absorption peak at the wavenumber of 1600 $cm^{-1}$ can be found in FIG. 1, which indicates the presence of USPIO.

Figure 2:
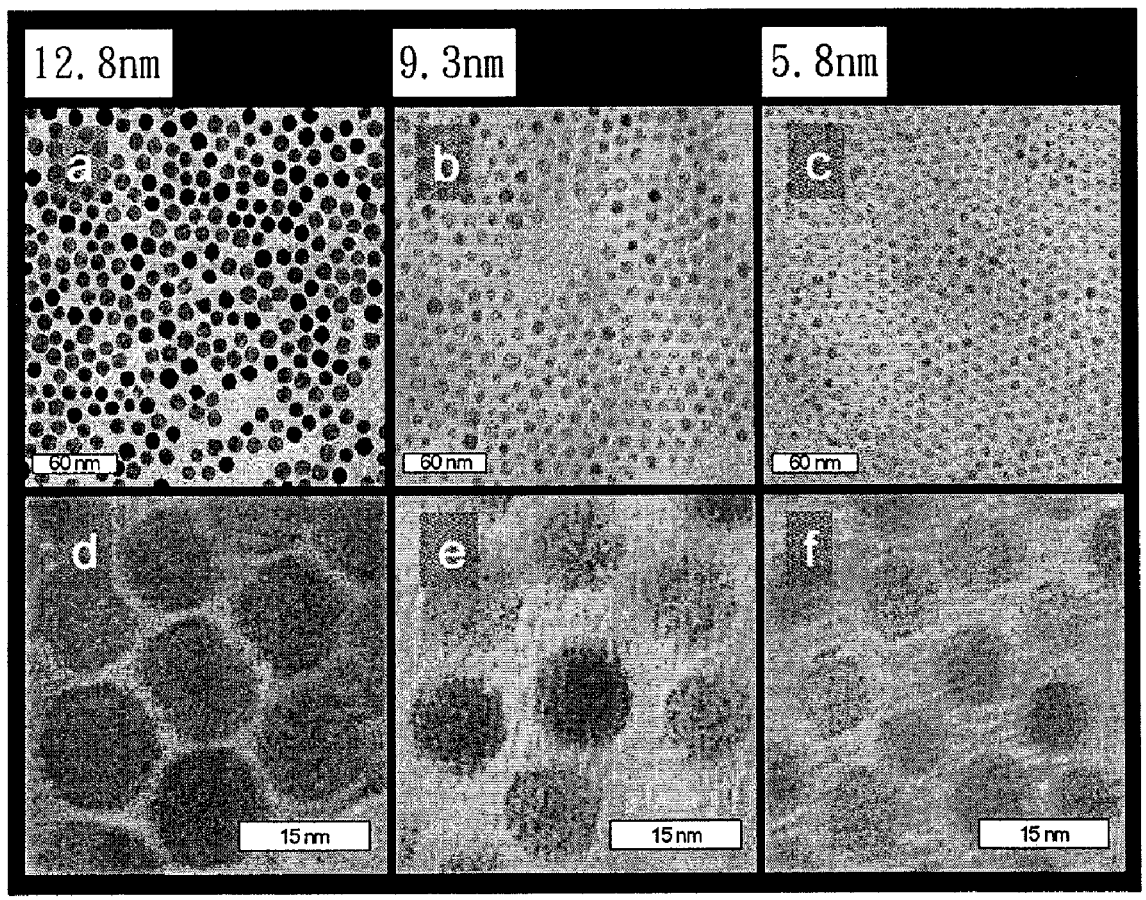
FIGS. 2 (d), (e) and (f) are the magnified images of FIGS. 2 (a), (b) and (c), respectively.

The configuration of the USPIO was determined by transmittance emission microscope (TEM, available from JEOL JEM Co., model name: 2000EXII). The microscopic results are shown in FIGS. 2(a) and 2(d). FIG. 2(d) is a magnified image of FIG. 2(a). The USPIO thus obtained has a particle size of about 12.8 nm and is round in shape. Measurements of the following properties of the USPIO were conducted using a superconducting quantum interference device (SQUID, available from QUANTUM DESIGN Co., Ltd., model name: MPMS5). The results show that the USPIO has a coercivity (Hc) of approximately 1 (an indication of exhibiting a superparamagnetic property), and a saturation magnetization of 279 emu/g.

It is noted that the particle size of the USPIO varies with the stirring speed during the mixing of $Fe(OA)_3$ and 1-octadecene (ODE). Experimental results analyzed by TEM show that the particle size of USPIO is about 9.3 nm when the stirring speed is 600 rpm (see FIGS. 2(b) and 2(e)) and is about 5.8 nm when the stirring speed is 900 rpm (see FIGS. 2(c) and 2(f)). Accordingly, the higher the stirring speed, the smaller will be the particle size of the USPIO.

2. Preparation of N-acryl-(3-aminopropyl)triethoxy silane (APTES-Ac)

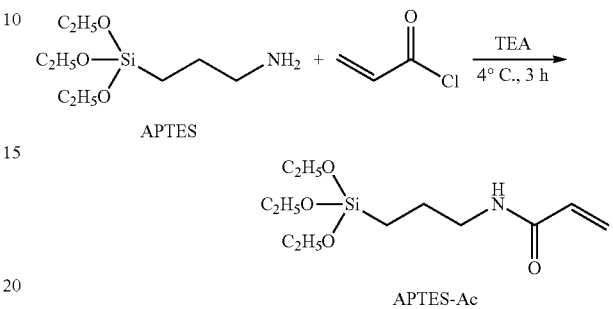

Figure 3:
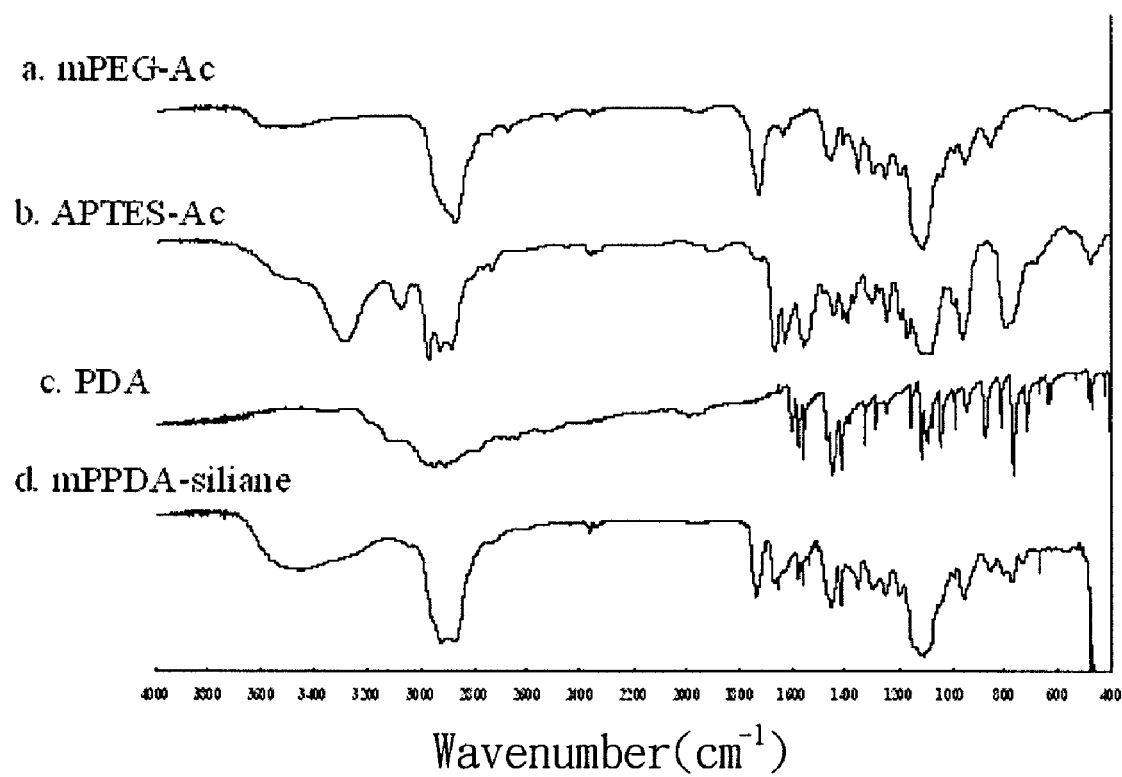
FIG. 3 shows FT-IR spectrums illustrating the functional groups in the structure of mPEG-Ac, APTES-Ac, PDA and mPPDA-silane prepared in Example 1 of this invention.

10.6 mL (45 mmol) of (3-aminopropyl)triethoxysilane (APTES) was dissolved in 300 mL of dry chloroform, followed by addition 12.9 mL (93 mmol) of triethylamine (TEA) therein so as to obtain a mixture. The mixture was mixed with 3.6 mL (45 mmol) of acryloyl chloride at 4° C. to form a reaction solution. The reaction solution was subjected to reaction at room temperature for 3 hours, followed by purification using column chromatography (eluent: $CHCl_3/C_2H_5OH=9/1$) to obtain a product of APTES-Ac. The FT-IR spectrum of the product is shown in FIG. 3.

3. Preparation of poly(ethylene glycol)acrylate (mPEG-Ac)

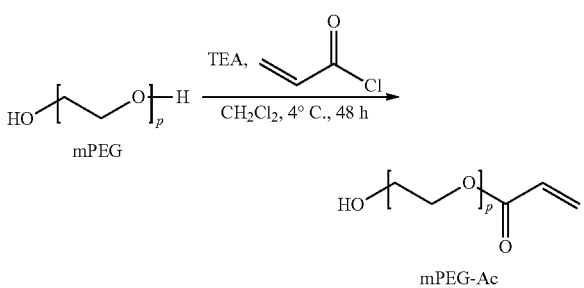

(p = 45)

75 g (100 mmol) of poly(ethylene glycol) was dried by heating at 90-100° C., and was then placed in a vacuum environment for 6 hours. 100 mL of dried $CH_2Cl_2$ and 27.7 g (200 mmol) of triethylamine (TEA) were added into the dried poly(ethylene glycol) to form a mixture. 10.8 mL (135 mmol) of acryloyl chloride was added dropwisely into the mixture at 4° C. to form a reaction solution, after which the reaction solution was subjected to reaction at room temperature for 48 hours, followed by heating and drying in a vacuum environment, educing of unreacted poly(ethylene glycol) by adding hexane, and precipitation of mPEG-Ac by adding tetrahydrofuran. The mPEG-Ac thus obtained was purified using column chromatography (eluent: $CHCl_3/C_2H_5OH=9/1$) to obtain a product of mPEG-Ac. The FT-IR spectrum of mPEG-Ac is shown in FIG. 3.

4. Preparation of 2-(pyridyldithio)-ethylamine (PDA)

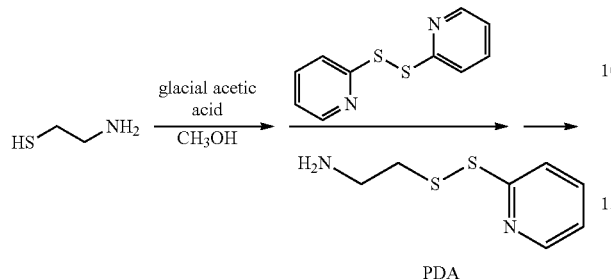

Figure 4:
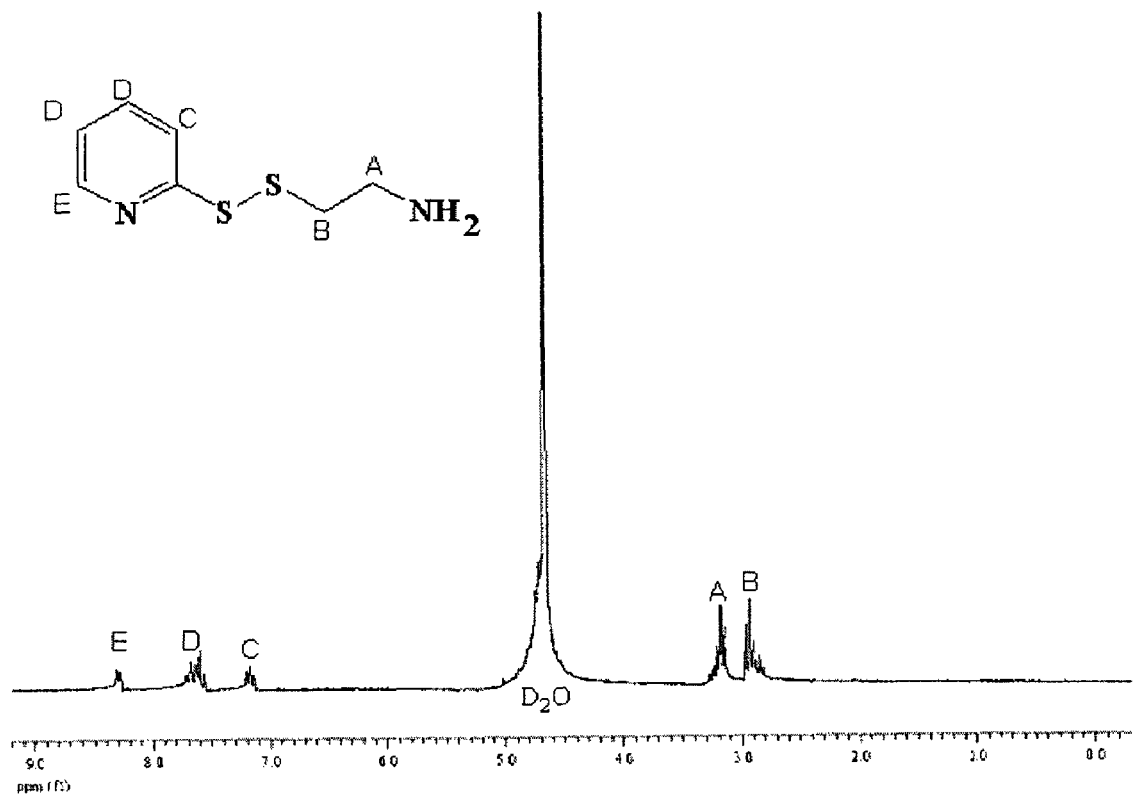
FIG. 4 is a $^1$H-NMR spectrum illustrating the structure of PDA in Example 1 of this invention.

PDA 2.288 g (20 mmol) of 2-mercaptoethylamine was dissolved in 17.5 mL of methanol, followed by mixing with 1.6 mL (26.7 mmol) of glacial acetic acid to form a mixture. 8.815 g (40 mmol) of 2,2'-dipyridyldisulfide was dissolved in 17.5 mL of methanol, followed by dropwise addition into the mixture to form a reaction solution. The reaction solution was subjected to reaction under a nitrogen gas environment for 48 hours, followed by evaporation to remove methanol and obtain a yellow grease. The grease was dissolved in 20 mL of methanol, followed by addition of 100 mL of ether. Addition of ether was repeated six times to obtain a precipitate of 1.95 g (8.8 mmol, 44% of yield) of white-powdery crystalline PDA-HCl. The PDA-HCl thus obtained was mixed with 2 mL of distilled water to form a mixture. An aqueous NaOH solution prepared by dissolving 384.7 g (9.6 mmol) of NaOH in 1 mL of distilled water was added quickly into the mixture under shaking for 15 minutes, followed by centrifuging for 15 minutes and removal of the upper layer to obtain a product of yellow oil PDA. $^1$H-NMR spectrum of the PDA thus obtained is shown in FIG. 4, and FT-IR spectrum of PDA thus obtained is shown in FIG. 3.

5. Preparation of N,N'-APTES-mPEG-PDA (mPPDA-silane)

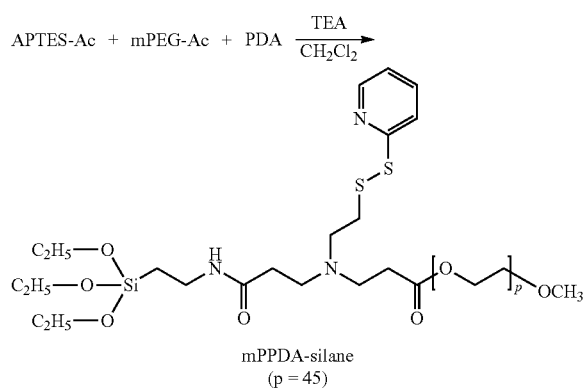

mPPDA-silane
(p = 45)

Figure 5:
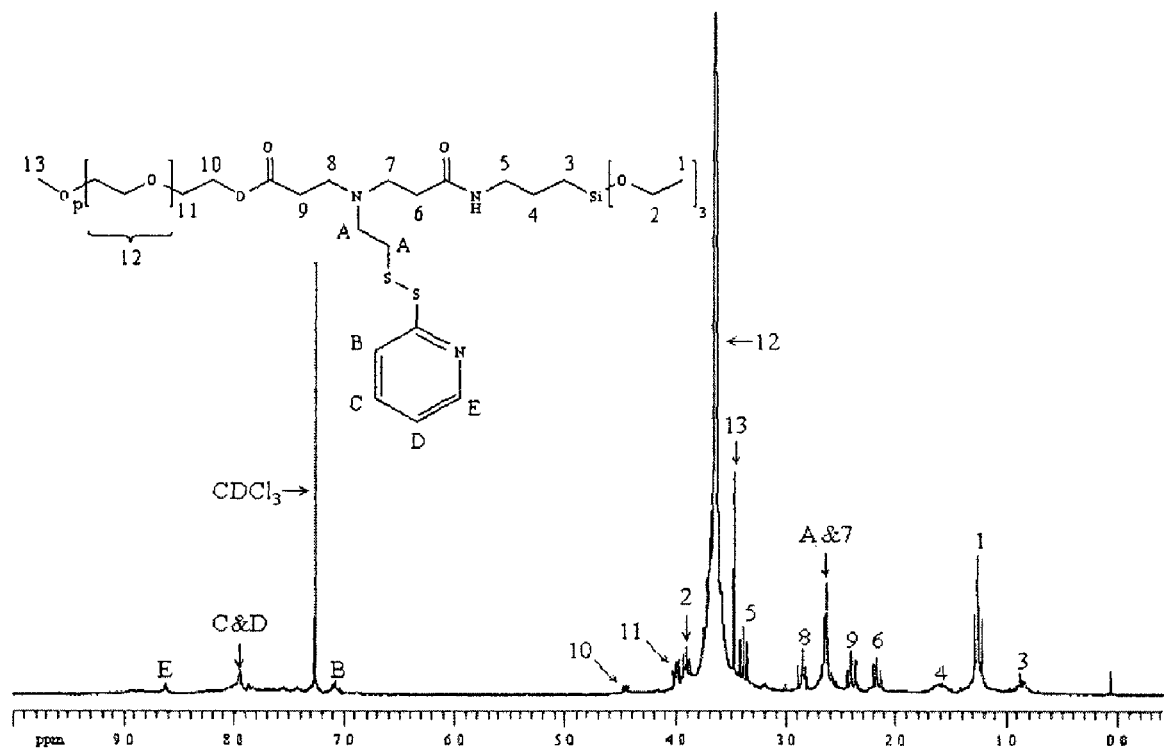
FIG. 5 is a $^1$H-NMR spectrum illustrating the structure of mPPDA-silane in Example 1 of this invention.

1.375 g (5 mmol) of APTES-Ac, 4 g (5 mmol) of mPEG-Ac and 0.93 g (5 mmol) of PDA were dissolved in 20 mL of dried CH$_2$Cl$_2$, after which the mixture was added with 0.693 mL (5 mmol) of triethylamine (TEA) to form a reaction solution. The reaction solution was subjected to reaction under a nitrogen gas environment for 72 hours, followed by addition of hexane and purification using column chromatography (eluent: CHCl$_3$/C$_2$H$_5$OH=9/1) to obtain a product of mPPDA-silane. The $^1$H-NMR spectrum of mPPDA-silane is shown in FIG. 5, and FT-IR spectrum of mPPDA-silane is shown in FIG. 3.

6. Preparation of USPIO-mPPDA

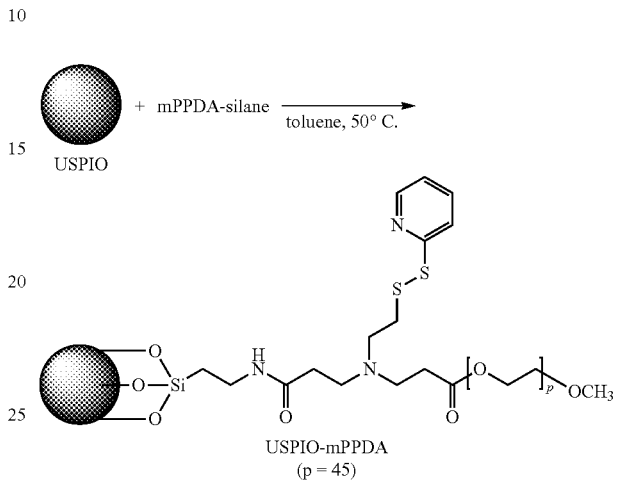

USPIO-mPPDA
(p = 45)

1 mmol of USPIO containing 56 mg of Fe and 1.3 g (1 mmol) of mPPDA-silane were dissolved in 20 mL of toluene to form a reaction solution. The reaction solution was heated to 50° C. under a nitrogen gas environment, after which the reaction solution was subjected to ultrasonic vibration for 6 hours, followed by addition of hexane so as to obtain a precipitate. The precipitate was dispersed in toluene and purified using a dialyzing membrane (Mn: 12,000~14,000) in secondary water to obtain a product of USPIO-mPPDA. The FT-IR spectrum of USPIO-mPPDA is shown in FIG. 1. The hydrated diameter of USPIO-mPPDA is about 29.9 nm determined using a dynamic light scattering (DLS) device (available from Malvern Instruments Co., model name: ZetaSizer 3000 HS$_A$).

Example 2

Preparation of USPIO-mPEG-RGD

1. Preparation of RGD-Cys

Rink Amide resin having Fmoc protecting groups at nitrogen end was placed in a solid phase peptide synthesizer. 20% of piperidine-DMF solution was added into the synthesizer and was allowed to pass through the resin for undergoing a de-protective step. Benzotriazole-1-yl-oxy-tris-pyrrolidino-phosphonium hexafluorophosphate (PyBOP) and 1-hydroxy-benzotriazole (HOBT) serving as coupling agents were dissolved in 0.4 M of N-methyl morpholine (NMM) serving as an activator to form a reagent, after which the reagent and Fmoc-Asp(O-tBu)-OH (Asp is an amino acid in the amino sequence of RGD-Cys; SEQ ID NO: 1) were charged into the synthesizer to subject the resin to graft reaction, so that Fmoc-Asp group was grafted with the resin. Then, acetic anhydride (Ac$_2$O) was added into the synthesizer to subject the nitrogen end of the resin that was not grafted with the amino acid to reaction. The above steps were repeated for five cycles until the amino sequence of RGD-Cys (SEQ ID NO: 1) was grafted with the resin. In each cycle, the modified resin was sampled for Kaiser test in order to determine whether each of the specific amino acids was grafted with the resin. 20% of piperidine in DMF was charged into the synthesizer to remove the Fmoc protective groups of the modified resin. The modified resin was then taken out of the synthesizer, and was washed with methanol for several times. The modified resin was purified by filtration and was dried in a vacuum environment.

Trifluoroacetic acid, water, triisopropyl silane and 1,2-ethanedithiol (EDT) in a volume ratio of 94.5/2.5/1/2.5 were mixed to form a reagent. The reagent and the modified resin were mixed under vibration for 2 hours, followed by washing the resin with methanol, filtering and collecting the filtrate, evaporating the filtrate until the volume of the filtrate was about 5 mL, adding ether into the filtrate to precipitate peptide (RGD-Cys; SEQ ID NO: 1), centrifuging for 5 minutes and taking the peptide out of the filtrate. The peptide was washed with methanol followed by precipitation using ether for 3.about.5 times. The precipitate was dissolved in de-ionized water and then freeze-dried to obtain RGD-Cys (SEQ ID NO: 1).

2. Preparation of USPIO-mPEG-RGD

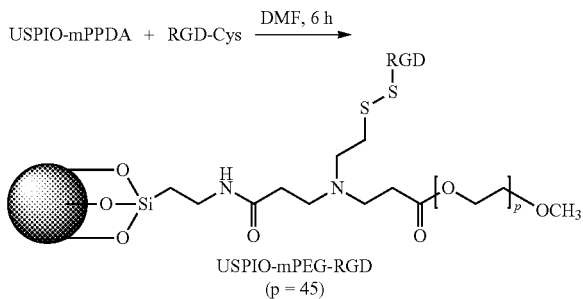

1.1 mg (20.mu.mol) of USPIO-mPPDA and 13.5 mg (20 μmol) of RGD-Cys (SEQ ID NO: 1) were dissolved in 5 mL of DMF to form a reaction solution. The reaction solution was subjected to reaction under a nitrogen gas environment for 6 hours, after which a trace amount of the above reaction solution was sampled and was analyzed by UV-VIS spectrometer. The results show that an absorptive peak at 343 nm, which corresponds to 2-mercaptopyridine (2-MP), is found in UV-VIS spectrum. Formation of 2-mercaptopyridine proves that RGD-Cys (SEQ ID NO: 1) is coupled to USPIO-mPPDA. Finally, the reaction solution was purified using a dialyzing membrane (Mn: 12,000.about.14,000) in secondary water to obtain a product of USPIO-mPPDA-RGD.

The hydrated diameter of the product is about 36.5 nm, which is about 6.6 nm longer than that of USPIO-mPPDA.

[TEST]

Figure 6:
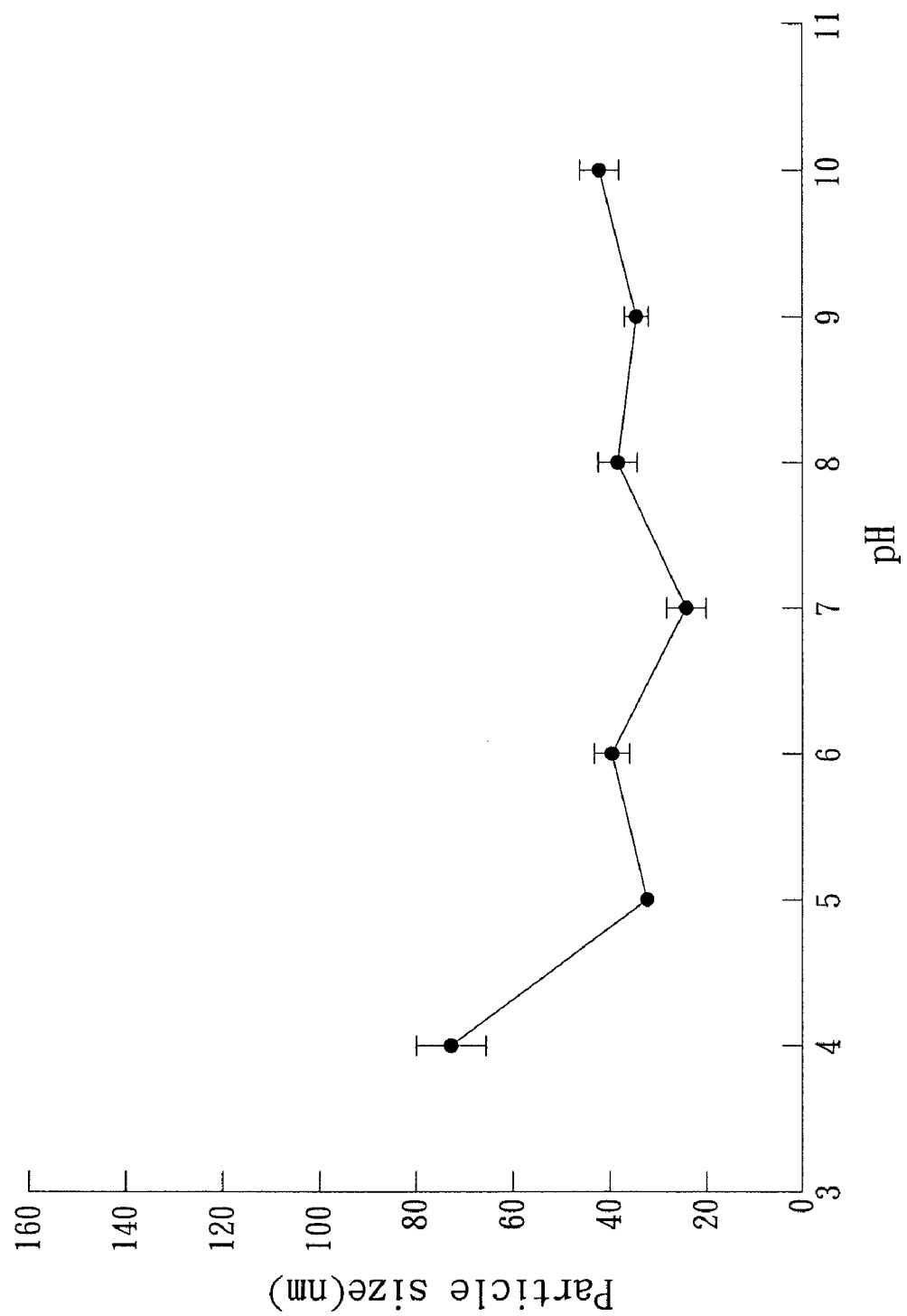
FIG. 6 is an analysis plot illustrating the variation of the particle size of USPIO-mPEG-RGD in solutions each having a specific pH value.

1. Dispersion:

The product of Example 2 was divided into several parts. Each part of the product was added in a solution having a pH value of 4~10, followed by monitoring in a DLS device to observe the variation of the particle size of the product. The results thus obtained are shown in FIG. 6.

The results show that the product of Example 2 is stable and highly dispersive in a solution having a pH value of 4~10. Furthermore, the results shown in FIG. 6 demonstrate that the particle size of the product remains substantially the same under a pH value of 5~10. Hence, the product of Example 2 can be easily coupled to the targeted tissue.

2. Surface Potential:

The surface potentials of USPIO-mPEG and USPIO-mPPDA of Example 1 and the product of Example 2 were measured using a surface potential meter.

Figure 7:
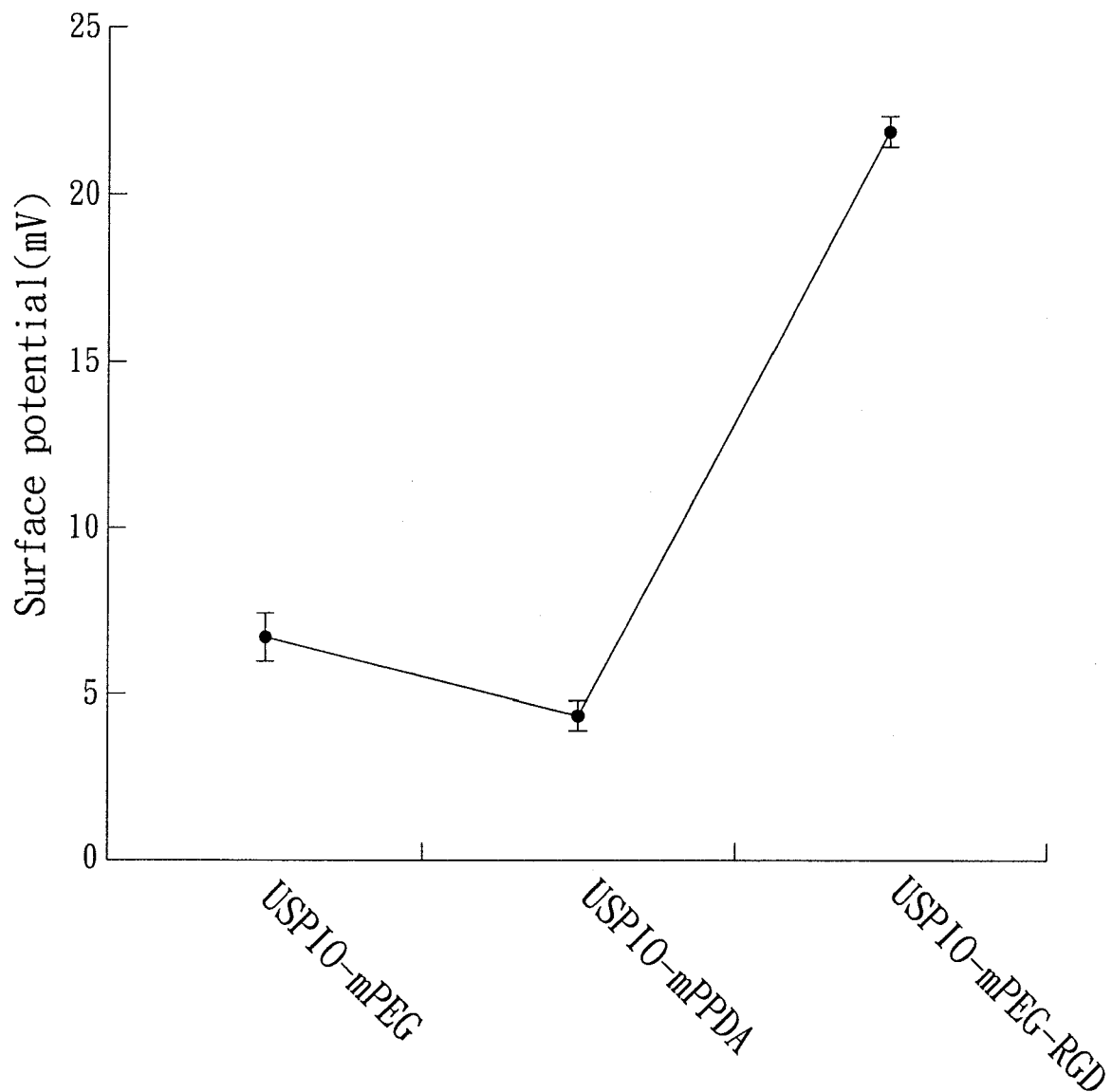
FIG. 7 is an analysis plot illustrating the surface potential of USPIO-mPEG and USPIO-mPPDA in Example 1, and that of USPIO-mPEG-RGD in Example 2.

As shown in FIG. 7, the measured results show that USPIO-mPPDA has a surface potential of 4.3 mV, while the product of Example 2 has a surface potential of 21.8 mV.

3. Protein Assay:

Four different solutions were placed in four colorimetric tubes A~D, respectively, to undergo protein assay test. The test results are as follows.

Tube A: containing a solution of BCA protein assay reagent (available from PIERCE, U.S.A.) serving as a blank. The tube A is colorless.

Tube B: containing a solution prepared by adding fetal bovine serum albumin standard reagent into the BCA protein assay reagent. The tube B has a color of purple, which indicates the presence of protein in the solution of tube B.

Tube C: containing a solution prepared by adding the reaction solution obtained from the preceding section, entitled "Preparation of USPIO-mPEG-RGD" of Example 2, to the BCA protein assay reagent, the color of the solution being gradually changed from light brown to purple during addition of the reaction solution to the BCA protein assay reagent, which indicates the presence of protein in the solution of tube C, i.e., an indication of forming the USPIO-mPEG-RGD in Example 2.

Tube D: containing a solution prepared by adding USPIO-mPPDA obtained from Example 1 to the BCA protein assay reagent, the color of the solution remaining light brown during addition of USPIO-mPPDA to the BCA protein assay reagent, which indicates absence of protein in the solution of tube D.

4. Cytotoxicity Study of USPIO-mPEG-RGD:

Five USPIO-mPEG-RGD solutions having concentrations of 100, 250, 500, 750 and 1000 μM, respectively, were prepared by mixing USPIO-mPEG-RGD of Example 2 and water for cytotoxicity test.

Each of five cell lines [cell line KB exhibits no expression of integrin receptor; cell lines MCF-7, HT-29, A549 and HT-1080 exhibit specified expression of integrin receptor, and are available from Bioresource Collection and Research Center (BCRC), R.O.C., and the cell number of each of five cell lines is $10^3$] was mixed with a respective one of the above USPIO-mPEG-RGD solutions to form a sample. The sample was incubated at 37.0±0.1° C. for 1 hour, followed by measuring the cell viability of the sample with MTT method. The results thus obtained are shown in FIG. 8.

Figure 8:
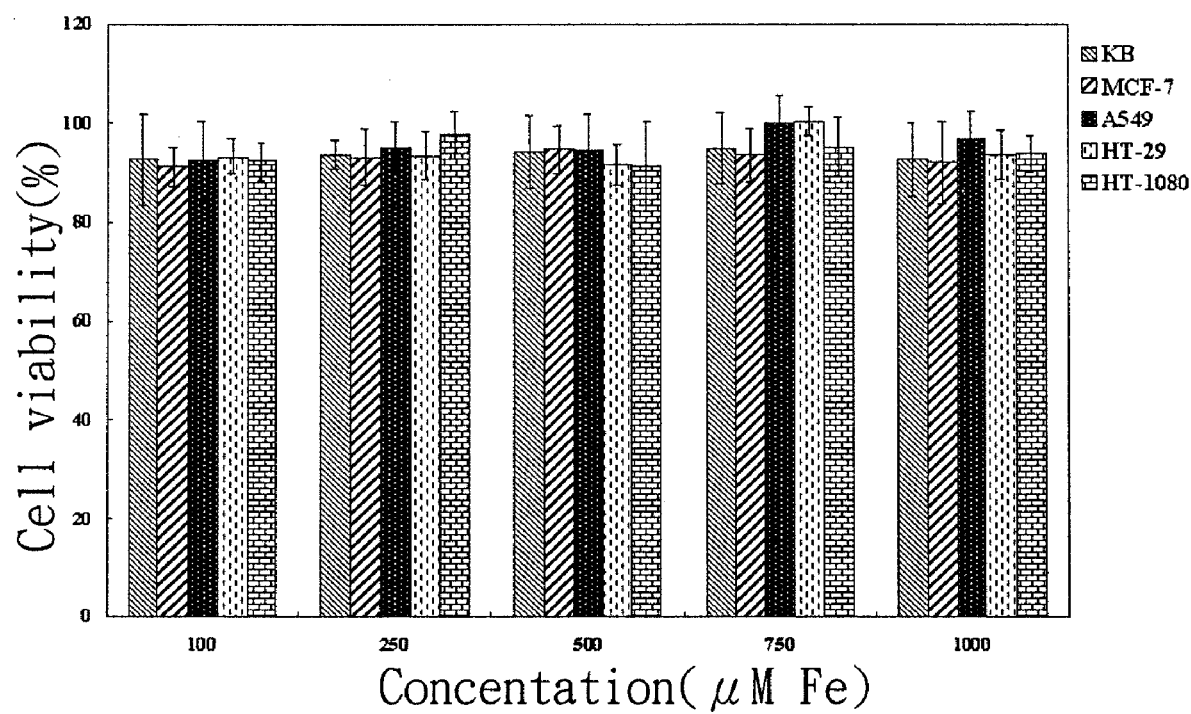
FIG. 8 is a bar chart illustrating the result of the cytotoxicity of USPIO-mPEG-RGD solution at different concentrations.

In FIG. 8, the cell viability of each of the samples is higher than 90%, which indicates that USPIO-mPEG-RGD has no cytotoxicity to cell line.

5. Tube Image Study of USPIO-mPEG-RGD:

Three USPIO-mPEG-RGD samples having different particle sizes of 12.8, 9.3 and 5.8 nm of USPIO, respectively, were prepared. Each of the USPIO-mPEG-RGD samples was formulated with different amounts of water to form five solutions having concentrations of 400, 200, 100, 50 and 25 μM, respectively. The 15 samples were placed in a box that was full of water, and was secured by Styrofoam, followed by scanning using T2-weighted image of MRI scanner. The black and white images shown on the left-hand side of FIG. 9 are the results of the scanning, and the images shown on the right-hand side of FIG. 9 are obtained by color processing of the images of the left-hand side.

Figure 9:
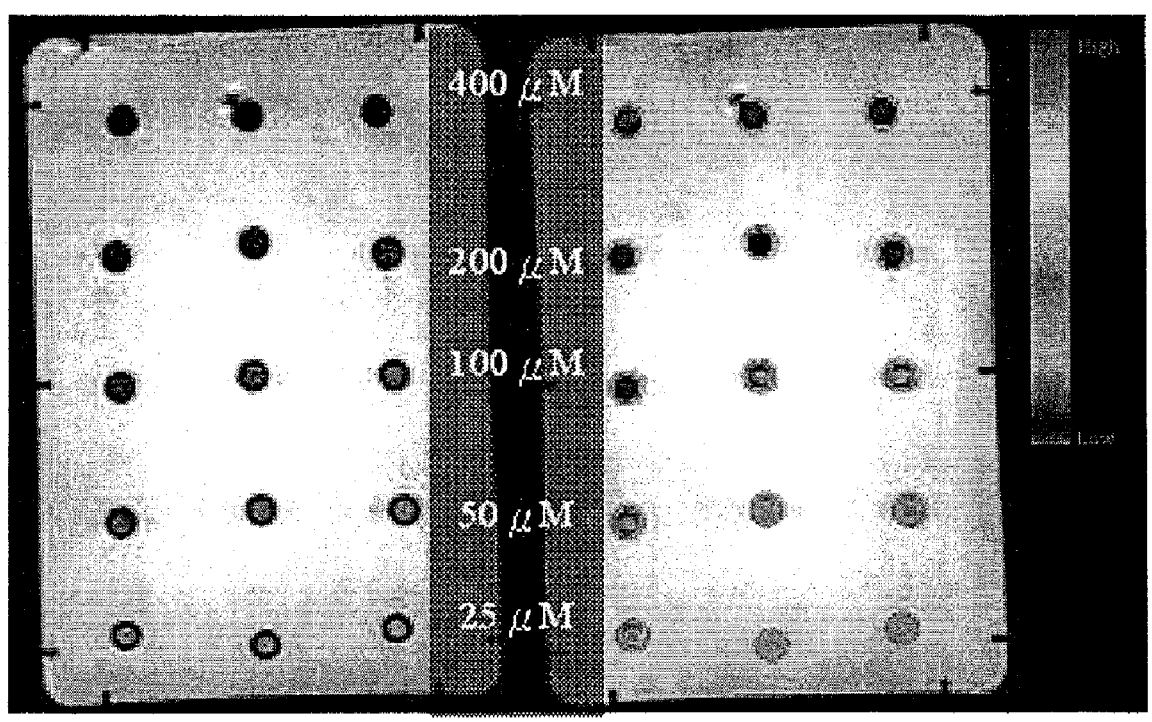
FIG. 9 is an image illustrating the result of a tube image study of USPIO-mPEG-RGD.

FIG. 9 shows that the sensitivity of T2-weighed image on the USPIO-mPEG-RGD is high, which indicates that the USPIO-mPEG-RGD is useful as a MRI contrast agent. FIG. 9 further shows that there is substantially no sensitivity on the image contrast for the USPIO-mPEG-RGD prepared from USPIO having a particle size of 5.8 nm when the concentration of the solution is less than 50 μM and for the USPIO-mPEG-RGD prepared from USPIO having a particle size of 9.3 nm when the concentration of the solution is less than 25 μM, and that there still remains a slight sensitivity on the image contrast for the USPIO-mPEG-RGD prepared from USPIO having a particle size of 12.8 nm when the concentration of the solution is less than 50 μM. As stated above, the larger the particle size of USPIO, the better will be the sensitivity on the image contrast.

6. In Vitro Image Study of USPIO-mPEG-RGD:

Each of five cell lines [cell line KB serving as a control; cell lines MCF-7, HT-29, A549 and HT-1080 each serving as an experiment and having an over expression of integrin receptor], was mixed with USPIO-mPEG-RGD, after which the mixture was incubated at 37.0±0.1° C. for 1 hour, followed by washing with phosphate buffer saline (PBS) and repeating the washing three times to obtain a sample. The samples and the five cell lines serving as blank samples were subjected to scanning using T2-weighted image of a MRI scanner (3.0T). The results thus obtained are shown in FIG. 10.

Figure 10:
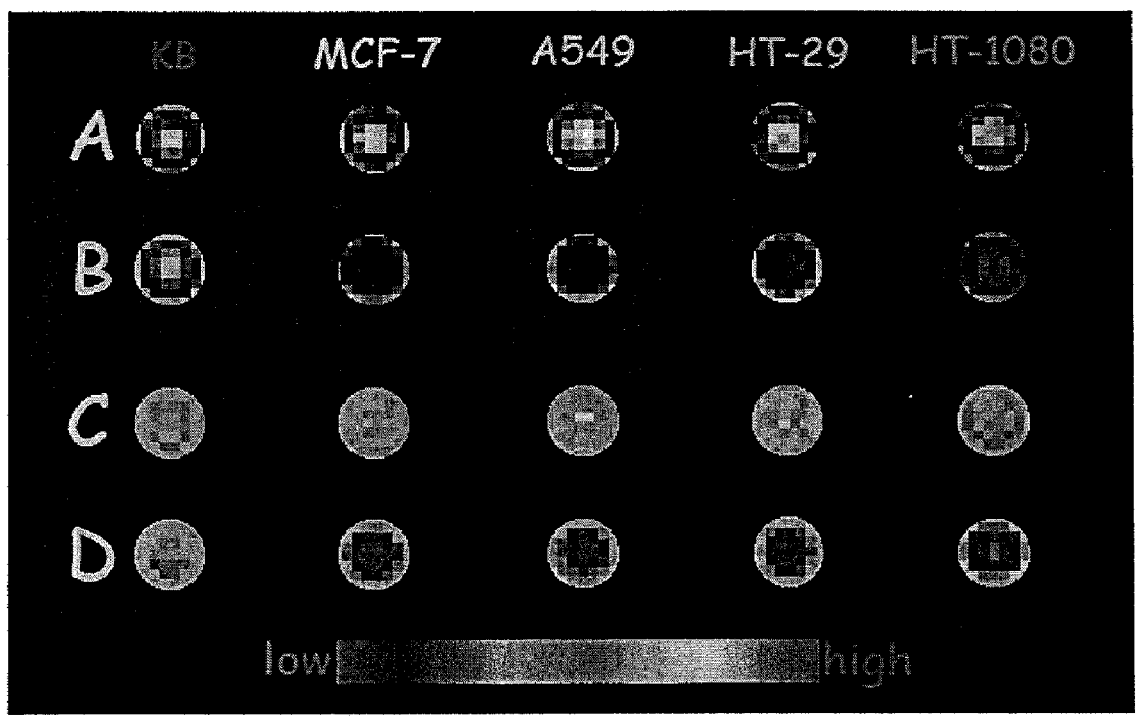
FIG. 10 is a photo illustrating the result of in vitro image study of USPIO-mPEG-RGD.

In FIG. 10, line A includes the images of blank samples, line B includes the images of the samples, line C includes the images obtained by color processing of the images of line A, and line D includes the images obtained by color processing of the images of line B. The difference between the image of each blank sample of line A and the image of the corresponding sample of line B or between the image of each blank sample of line C and the image of the corresponding sample of line D is apparent (i.e., the image signals of the samples of MCF-7, A549, HT-29, and HT-1080 were reduced in line B or line D), which proves that USPIO-mPEG-RGD can be used for detecting the cell exhibiting the expression of integrin receptor. Moreover, the images of the five samples are different from each other, which indicates that USPIO-mPEG-RGD can target different cell lines exhibiting different expressions of integrin receptor.

Figure 11:
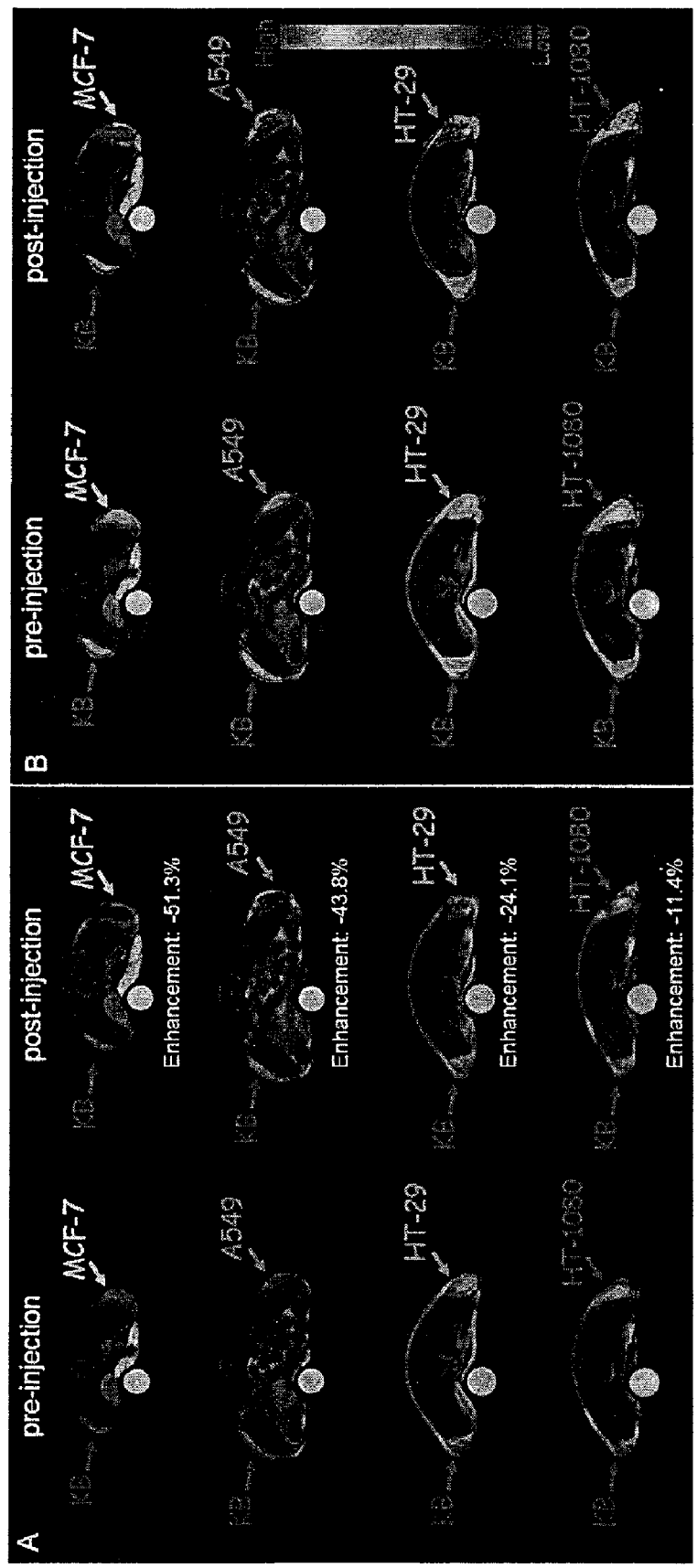
FIG. 11 is a photo illustrating the result of in vivo image study of USPIO-mPEG-RGD.

7. In Vivo Image Study of USPIO-mPEG-RGD:

Each of five cell lines [cell line KB serving as a control; and cell lines MCF-7, HT-29, A549 and HT-1080 serving as experiments] was injected into the hind legs of each of five rats (available from the foundation of National Laboratory Animal Center, R.O.C.). After one week, each of the five rats was subjected to scanning using a whole body MRI scanner (3.0 T), the images thus obtained are shown in FIG. 11 (see the images in the lines called "pre-injection").

Then, 20 μmol/Kg of USPIO-mPEG-RGD was injected into the tail of each of the rats, followed by scanning using a whole body MRI scanner (3.0T) after half an hour. The images thus obtained are also shown in FIG. 11 (see the images in the lines called "post-injection"), in which the images on the left-hand side A of FIG. 11 are the scanning images thus obtained, and the images on the right-hand side B of FIG. 11 are obtained by color processing of the images of the left-hand side A.

The image signal variations between pre-injection and post-injection for the cell lines MCF-7, A549, HT-29 and HT-1080 are 51%, 44%, 24% and 11%, respectively, which indicates that USPIO-mPEG-RGD can be targeted to different cell lines exhibiting different expressions of integrin receptor.

In conclusion, the nanoparticles of this invention exhibit a high targeting property, and high saturation magnetization, and are highly dispersive in water.

While the present invention has been described in connection with what are considered the most practical and preferred embodiments, it is understood that this invention is not limited to the disclosed embodiments but is intended to cover various arrangements included within the spirit and scope of the broadest interpretation and equivalent arrangements.

What is claimed is:

1. A nanoparticle comprising:
a core including superparamagnetic nanoparticles and having an outer surface; and
siloxanyl moieties covalently coupled to said outer surface of said core and having Formula (I):

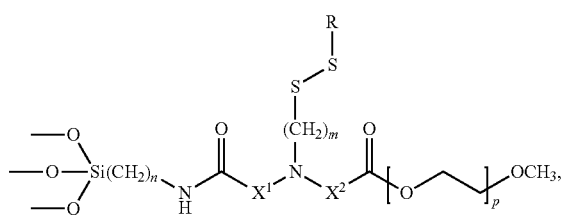

wherein, in Formula (I): $X^1$ and $X^2$ independently represent methylene, ethylene or propylene;

R represents an optionally substituted pyridyl group, or
—S—R is a group derived from a targeting ligand containing —SH group and effective to bind specifically with a predetermined targeted cell in an object;

n and m independently represent an integer ranging from 1 to 3; and p represents an integer ranging from 9 to 45.

2. The nanoparticle of claim 1, wherein R represents a substituted or unsubstituted pyridyl group selected from the group consisting of 2-pyridyl, 4-pyridyl, 5-methyl-2-pyridyl, 3-methyl-2-pyridyl, and 1-methyl-2-pyridyl.

3. The nanoparticle of claim 2, wherein R is 2-pyridyl.

4. The nanoparticle of claim 1, wherein said targeting ligand is a targeting peptide sequence.

5. The nanoparticle of claim 4, wherein said targeting peptide sequence is interleukin 11, modified bombesin containing —SH group, or (Cys-Lys-Gly-Arg-Gly-Asp) (SEQ ID NO: 1).

6. The nanoparticle of claim 1, wherein $X^1$ and $X^2$ independently represent ethylene, R is 2-pyridyl and n=m=2.

7. The nanoparticle of claim 5, wherein $X^1$ and $X^2$ independently represent ethylene, —S—R is a group derived from (Cys-Lys-Gly-Arg-Gly-Asp) (SEQ ID NO: 1).

8. A magnetic resonance imaging contrast agent adapted to be used in detecting living cells or tissues by magnetic resonance imaging techniques, comprising the nanoparticle of claim 1.

* * * * *

SEQUENCE LISTING

```
<160> NUMBER OF SEQ ID NOS: 1

<210> SEQ ID NO 1
<211> LENGTH: 6
<212> TYPE: PRT
<213> ORGANISM: Artificial Sequence
<220> FEATURE:
<223> OTHER INFORMATION: targeting ligand

<400> SEQUENCE: 1

Cys Lys Gly Arg Gly Asp
1               5
```